United States Patent
Jinka et al.

(10) Patent No.: US 9,131,668 B2
(45) Date of Patent: Sep. 15, 2015

(54) TUMOR MODEL SYSTEM USEFUL TO STUDY MULTISTAGE CANCER

(71) Applicant: COUNCIL OF SCIENTIFIC & INDUSTRIAL RESEARCH, New Delhi (IN)

(72) Inventors: Rajeswari Jinka, Hyderabad (IN); Gopal Pande, Hyderabad (IN)

(73) Assignee: Council for Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/029,331

(22) Filed: Sep. 17, 2013

(65) Prior Publication Data

US 2014/0093456 A1  Apr. 3, 2014

Related U.S. Application Data

(63) Continuation of application No. 12/935,884, filed as application No. PCT/IN2009/000213 on Mar. 31, 2009, now Pat. No. 8,563,306.

(30) Foreign Application Priority Data

Mar. 31, 2008 (IN) ............................. 845/DEL/2008

(51) Int. Cl.
*A61K 49/00* (2006.01)
*A01K 67/00* (2006.01)
*C12N 5/06* (2006.01)
*A01K 67/027* (2006.01)
*C12N 5/077* (2010.01)

(52) U.S. Cl.
CPC ............ *A01K 67/0271* (2013.01); *A61K 49/00* (2013.01); *A61K 49/0008* (2013.01); *A01K 2227/105* (2013.01); *A01K 2267/0331* (2013.01); *C12N 5/0656* (2013.01)

(58) Field of Classification Search
CPC .............. A61K 49/00; A61K 49/0008; A01K 67/0271; A01K 2227/105; A01K 2267/0331; C12N 5/0656
USPC ................................ 424/9.2; 435/353; 800/10
See application file for complete search history.

(56) References Cited

U.S. PATENT DOCUMENTS 7,053,263 B2  5/2006  Sawyers et al. .................... 800/9
2003/0219376 A1  11/2003  Fisher ........................... 424/1.49

FOREIGN PATENT DOCUMENTS

| WO | WO 91/01760 | 2/1991 |
| WO | WO 01/00677 | 6/2000 |
| WO | WO 03/075957 | 9/2003 |
| WO | WO 2006/074186 | 1/2006 |

OTHER PUBLICATIONS

Assoian et al, "Coordinate Signaling by Integrins and receptor tyrosine kinases in the regulation of G1 phase cell-cycle progression," *Curr Opin Genet Dev.*, 11(1):48-53, 2001.
Bonaccorsi et al, "Androgen receptor expression in prostate carcinoma cells suppresses alpha6beta4 integrin-mediated invasive phenotype," *Endocrinology*, 141(9):3172-82, 2000.
Hsu et al., "Integrin alpha v beta 3 antagonists for anti-angiogenic cancer treatment," *Recent Patents on Anti-Cancer Drug Discovery*, 2:143-158, 2007.
Hynes, "Integrins: Bidirectional allosteric signaling machines," *Cell*, 110:673-687, 2002.
Kalluri et al., "Fibroblasts in cancer," *Nature Reviews Cancer*, 6(5):392-401, 2006.
Kozlowski et al., "Metastatic behavior of human tumor cell lines grown in the nude mouse," *Cancer Research*, 44(8):3522-3529, 1984.
Ledezma et al., "Apoptotic and anti-adhesion effect of ajoene, a garlic derived compound, on the murine melanoma B16F10 cells: possible role of caspase-3 and the alpha(4)beta(1) integrin," *Cancer Letters*, 206:35-41, 2004.
Lodish et al, Molecular Cell Biology. 4th. New York: W.H. Freeman and Company, pp. 751-792, 817-822, 970-988 and 1056-1082, 2000.
McGill et al., "Loss of matrix adhesion triggers rapid transformation-selective apoptosis in fibroblasts," *Journal of Cell Biology*, 138:901-911, 1997.
Rajeswari et al., "Direct association between caspase 3 and alpha5beta1 integrin and its role during anoikis of rat fibroblasts," *Cell Biol. Int.*, 30:963-969, 2002.
Rajeswari et al., "The significance of alpha 5 beta 1 integrin dependent and independent actin cytoskelton organization in cell transformation and survival," *Cell. Biol. Int.*, 26:1043-1055, 2002.
Ruoslahti et al., "The RGD story: a personal account," *Matrix Biology*, 22:459-465, 2003.
Rust et al., "The Promise of Integrins as Effective Targets for Anti-cancer Agents," *J Biomed Biotechnol.*, 124-130, 2002.
Seiki et al., "Role of pericellular proteolysis by membrane-type 1 matrix metalloproteinase in cancer invasion and angiogenesis," *Cancer and Metastasis Reviews*, 22(2): 129-143, 2003.
Stupack et al., "Integrins and angiogenesis," *Curr Top Dev Biol.*, 64:207-38, 2004.
Jinka et al., "Differential gene expression and clonal selection during cellular transformation induced by adhesion deprivation", *BMC Cell Biology*, 11:93-105, 2010.
Shimakage et al., "Tumorigenicity of EBNA2-transfected cells", *FEBS Letters*, 371:245-248, 1995.

(Continued)

*Primary Examiner* — Shin Lin Chen
(74) *Attorney, Agent, or Firm* — Norton Rose Fulbright US LLP (57) ABSTRACT

The present invention relates to a method of developing a Tumor Model System. The invention deals with a tumor model system with adhesion deprived cells. This observation provides a new method for primary detection of transformation of adhesion-deprived cells and tumorigenicity. The adhesion-deprived cells are capable of metastasizing at distant sites and the model system includes both the tumor formation and metastasis.

10 Claims, 10 Drawing Sheets

(56) References Cited

OTHER PUBLICATIONS

Chang et al., "Overexpression of Phospholipase C-y1 in Rat 3Y1 Fibroblast Cells Leads to malignant Transformation", *Cancer Research*, 57:5465-5468, 1997.

Tagawa et al., "Synergistic action of the microRNA-17 polycistron and Myc in aggressive cancer development", *Cancer Science*, 98(9):1482-1490, 2007.

Hamman et al., "Oral Delivery of Peptide Drugs: Barriers and Develpments", *Biodrugs*, 19(3):165-177, 2005.

Adherent cells

Figure 1 a

Adhesion deprived cells

Soft Agar Colony formation and Tumor formation in Nude mice:

Adherent cells

Figure 3a

Adhesion deprived cells

Figure 3b

Adherent cells

Figure 4a

*Adhesion deprived cells*

Tumor

Figure 5a

Lung

TUMOR MODEL SYSTEM USEFUL TO STUDY MULTISTAGE CANCER

This application is a Continuation of U.S. application Ser. No. 12/935,884 which is a national phase application under 35 U.S.C. 371 of International Application No. PCT/IN2009/000213 filed 31 Mar. 2009, which claims priority to Indian Application No. 845/DEL/2008 filed 31 Mar. 2008. The entire text of each of the above-referenced disclosures is specifically incorporated herein by reference without disclaimer.

FIELD OF THE INVENTION

The present invention relates to a method of developing a Tumor Model System. The invention deals with a tumor model system with adhesion deprived cells. This invention provides a new method for primary detection of transformation of adhesion-deprived cells and tumorigenicity. The adhesion-deprived cells are capable of metastasizing at distant sites and the model system includes both the tumor formation and metastasis.

BACKGROUND OF THE INVENTION

Cell matrix and cell-cell interactions are important physiological determinants of cell growth, survival and transformation. Cell adhesion to extra cellular matrix (ECM) via integrins also crucially influences the organization of cytoskeleton. Ligand binding to integrins leads to integrin clustering and recruitment of actin filaments and signaling proteins to the cytoplasmic domain of integrin (Hynes, R. O., 2002. Integrins: Bidirectional, allosteric signaling machines. Cell. 110, 673-687). These complexes provide outside in signaling to regulate diverse cellular functions balancing survival and death pathways in both normal and tumorigenic cells (Assoian R K, Schwartz M A. 2001. Coordinate signaling by integrins and receptor tyrosine kinases in the regulation of G1 phase cell-cycle progression. Curr Opin Genet Dev. 11(1): 48-53). Most of the adhesion dependent cells undergo apoptosis after deprivation of substratum. Integrin ligation can rescue these cells, which demonstrate that integrins are involved in stimulating apoptosis resistant mechanisms and allow the ceils to undergo transformation (Rajeswari, J and Pande, G. 2002. The significance of $\alpha 5\beta 1$ integrin dependent and independent cytoskeleton organization in cell transformation and survival. Cell Biol. Int. 26, 1043-1055). Integrins also provide signals to detach from primary tumors, to invade and colonize at secondary sites during metastasis (Lodish, H., Berk, A., Zipursky, S. L., Matsudaira, P., Baltimore, D., and Darnell, J. 2002. Molecular Cell Biology 4th ed., W.H. Freeman and Company, New York, pp. 751-792, 817-822, 970-988, 1056-1082 and Seiki, M., Koshikawa, N., Yana, I., 2003. Role of pericellular proteolysis by membrane-type1 matrix metalloproteinase in cancer invasion and angiogenesis. Cancer and Metastasis Reviews. 22 (2), 129-143, Ledezma, 2004) and angiogenesis (Stupack D G, Cheresh D A. Integrins and angiogenesis. 2004 Curr Top Dev Biol. 64, 207-38.). In contrast, some cancerous cells die rather than to colonize at distant sites (Rust et. al., 2002). Hence changes in the integrin expression profiles may dramatically influence the progression of malignant tumors by inducing various signaling molecules such as Jun kinases (JNKs), p38-kinase, Bad and various caspases.

Several recent studies have shown the effectiveness of integrins as indicators of diseases such as cancer and angiogenesis. Both up regulation and down regulation of integrin expression could serve as effective markers in cancer detection. For e.g. down regulation of $\alpha 6$ and $\beta 4$ may contribute to higher tumorigenesis in prostate cancer cells (Bonaccorsi L, Carloni V, Muratori M, Salvadori A, Giannini A, Carini M, Serio M, Forti G, Baldi E. 2000 Endocrinology. 141(9), 3172-82). Androgen receptor expression in prostate carcinoma cells suppresses alpha6beta4 integrin-mediated invasive phenotype. The clinical correlations of patient biopsies to integrin expression are recapitulated to some degree in rodent and in vitro analyses. For example, a study of rat hepatocarcinogenesis showed that integrins $\alpha 1$ and $\alpha 5$ were up-regulated in metastases of the lung and diaphragm, while integrins $\alpha 1$, $\alpha 2$, $\alpha 3$, and $\alpha 5$ were decreased in the primary carcinoma and preneoplastic nodules (Rust W L, Carper R S and Plopper G E. 2002. The promise of integrins as effective targets for anticancer agents. J Biomed Biotechnol. 2002; 124-130).

The regulatory mechanisms of cell survival and apoptosis are very complex in nature, implicating numerous players and signaling pathways not only in the decision-making process of surviving (or dying), but as well as in the execution of apoptosis itself. The same complex nature applies with regards to anoikis, a form of apoptosis that is largely regulated by integrin-mediated cell-extracellular matrix interactions.

Majority of cancer-related deaths are associated with metastasis. The metastatic cascade is a complex process consisting of a number of important steps that include loss of tissue architecture, local invasion, invasion into blood and lymph vessels, extravasation, establishment of the secondary foci and angiogenesis. Invasion of the extracellular matrix and metastatic spread of cancer to other tissues is also likely to reflect the ability of tumour cells to digest their surrounding matrix scaffold through secretion of matrix-degrading enzymes such as matrix metalloproteinases (MMPs). Invasion of the extracellular matrix and metastatic spread of colon cancer is also likely to reflect the ability of tumour cells to digest their surrounding matrix scaffold through secretion of matrix-degrading enzymes such as matrix metalloproteinases (MMPs). The mechanisms whereby human colon cancer cells escape the constraints on growth imposed on normal cells by cell crowding and dense pericellular matrices isomclear. However, the mechanisms whereby tumorigenic cells escape the constraints on growth imposed on normal cells by cell crowding and dense pericellular matrices is unclear (A method of modulating integrin mediated cellular activity and agents useful for same. 2001. WO/2001/000677).

DESCRIPTION OF THE PRIOR ART

Cancer is a serious disease and a major killer. Although there have been advances in the diagnosis and treatment of certain cancers in recent years, there is still a need for a development of a model system, which helps in understanding the nature of cancer and is useful in screening different types of drugs. The present invention relates to transformation and in particular to cancer.

Many reports showed that the integrins play a crucial role in treatment of cancer. The integrins that bind to RGD peptides are generally over-expressed in angiogenic vessels, including those of tumors and in inflammatory lesions, such as rheumatoid arthritis. In some tumors, the tumor cells also express RGD-binding integrins. A vast body of preclinical and clinical literature exists on the use of RGD-based integrin antagonists in cardiovascular disease and cancer. (Ruoslahti, E. 2003. RGD story: A personal account. A Landmark Essay. Matrix Biology. 22: 459-465).

Throughout the past decade, numerous patents have been published and issued using $\alpha v\beta 3$ antagonists for the prevention and/or treatment of cancer, with many antagonists demonstrating positive pre-clinical anti-angiogenic and anti-tumor results, which use antibodies, RGD peptides, non-RGD peptides, peptidomimetics. (Hsu et. al. 2007. Integrin αvβ3 antagonists for Anti-angiogenic cancer treatment. Recent Patents on Anti-Cancer Drug Discovery, 2, 143-158)

The invention in WO/2003/075957 provides methods for identifying antagonist of Integrin a vβ3, particularly for antibodies that specifically bind to the same epitope as Vitaxin (E and/or LM609. as Vitaxin (E and/or LM609) (Patent no. (WO/2003/075957) The prevention or treatment of cancer using integrin alpha v beta3 antagonists in combination with other agents).

However, very few model systems showed in literature, where prostate cancer progression is shown in immune deficient mouse with human prostate xenograft (Sawyers et. al., 2006. Mouse models of human prostate cancer progression. U.S. Pat. No. 7,053,263).

An autochthonous mouse model of bladder cancer that originates in the urothelium and ultimately progresses to invasive disease. This was accomplished by using adenovirus-Cre delivery system to achieve sporadic deletion of tumor suppressor function (*Cory Abate-Shen, 06-38 UMDNJ) Research Tool*).

Current invention includes the primary detection of transformation by soft agar colony formation and their efficiency in forming tumors indicated by tumorigenicity in nude mice.

OBJECTS OF THE INVENTION

The main object of the present invention is to obtain an animal tumor model system.

Another object of the present invention is to provide a method of preparation of the model system.

Still another object of the present invention is development of tumors in particular sarcomas, derived from adhesion deprived cells.

Still another object of the present invention is detection of metastasis in the model system.

Yet another object of the present invention is use of the model system for developing anti tumor therapies.

Still another object of the present invention is use of the model system to study the progression of cancer at their multistage.

DEFINITIONS

Metastasis (Greek: displacement, μετά=next+ στάτς=placement, plural: metastases), sometimes abbreviated mets, is the spread of a disease from one organ or part to another non-adjacent organ or part. Only malignant tumor cells and infections have the capacity to metastasize. Metastatic disease is a synonym iof metastasis.

Cancer cells can "break away", "leak", or "spill" from a primary tumor, enter lymphatic and blood vessels, circulate through the bloodstream, and settle down to grow within normal tissues elsewhere in the body. Metastasis is one of three hallmarks of malignancy (contrast benign tumors). Most tumors and other neoplasms can metastasize, although in varying degrees (e.g., glioma and basal cell carcinoma rarely metastasize).

When tumor cells metastasize, the new rumor is called a secondary or metastatic tumor, and its cells are like those in the original tumor. This means, for example, that if breast cancer metastasizes to the lung, the secondary tumor is made up of abnormal breast cells, not of abnormal lung cells. The tumor in the lung is then called metastatic breast cancer, not lung cancer.

Anoikis is a form of programmed cell death which is induced by anchorage-dependent cells detaching from the surrounding extracellular matrix (ECM). Usually cells stay close to the tissue to which they belong since the communication between proximal cells as well as between cells and ECM provide essential signals for growth or survival. When cells are detached from the ECM, i.e. there is a loss of normal cell-matrix interactions, they may undergo anoikis. However, metastatic tumor cells may escape from anoikis and invade other organs.

The term "neoplastic cell" s to be taken to mean a cell exhibiting abnormal growth and may or may not be a malignant cell. "Growth" is to be taken in its broadest sense and includes proliferation of the cell. In this regard, an example of abnormal cell growth is the uncontrolled proliferation of a cell.

The term angiogenesis, is a process of developing new blood vessels. Angiogenesis is important in the normal development of the embryo and fetus. It also appears important to tumor formation. Certain proteins, including angiostatin and endostatin, secreted by tumors work (at least in mice), by interfering with the blood supply tumors need.

The term peptide means a small piece of protein consisting of a linear molecule made up of two or more amino acids (the building blocks of proteins) linked by peptide bonds.

SUMMARY OF THE INVENTION

Accordingly the present invention relates to a method of developing a tumor model system to study the efficiency of growth and drug treatment at multistage of cancer. Cell matrix and cell-cell interactions are important physiological determinants of cell growth, survival and transformation. Normal adherent cells lose their viability rapidly when deprived from cell adhesion. Adhesion deprived cells are different physiologically and morphologically when compared with normal adherent cells and show the characteristics of transformation (Rajeswari, J and Pande, G. 2002. The significance of α5β1integrin dependent and independent cytoskeleton organization in cell transformation and survival. Cell Biol. Int. 26, 1043-1055 & J. Rajeswari, and Gopal Pande. 2006. Direct association of α5β1 integrins with caspase 3. Cell Biol Int., 30, 963-969).

In our current invention the cells that are changing their morphology phenotypically and physiologically show variation in transformation efficiency with the different time points of adhesion deprivation. This was confirmed by growing the cells into colonies in soft agar and by forming tumors when injected into immunocompromised nude mice. Further, the adhesion-deprived cells have the capacity to metastasize to distant organs from the site of injection.

In an embodiment of the present invention a method of preparing an animal rumor model system comprising:
 a. preparing adhesion deprived cells by trypsinizing normal adherent rat fibroblast cells, F111;
 b. suspending the said adhesion deprived rat fibroblast cells (F111) of step 'a' on 0.8 to 1% agarose coated surface in Dulbecco's Modified Eagle's medium containing 8 to 10% Foetal Calf Serum (FCS) to obtain adhesion deprived transformed fibroblast cells;
 c. administering subcutaneously the said transformed adhesion deprived cells of step 'b' into an immunocompromised mammal; and d. allowing the adhesion deprived cells of step 'c' to metastasize in the immunocompromised mammal for a period of about 4 weeks to about 6 weeks after in vivo transformation to obtain the animal tumor model system.

In an embodiment of the present invention, the in vitro transformation of non adherent cells of step is confirmed by a soft agar colony formation assay.

In an embodiment of the present invention, the detection of localization of metastasis in the method of preparing an animal tumor model system comprises:
  i. collecting tissue samples from organs selected from a group consisting of tumor, lung, spleen and kidney of the model system;
  ii. paraffin embeding of the sections of the said tissues of step (i) by known process;
  iii. staining paraffin sections of step (ii) with Haematoxylin and Eosin;
  iv. detecting metastasis in the stained paraffin sections of step (iii) by differential staining pattern of neoplastic cells and their penetration in the localized tissue.

In an embodiment of the present invention, harvesting adhesion-deprived cells on 0.8% agarose coated surfaces and the cell viability of the cells drops as the period of adhesion deprivation increases In an embodiment of the present invention, FCS used is about 8 to 10%.

In an embodiment of the present invention, the NA cells are mixed with 0.2-0.3% of agarose in serum containing DMEM medium and overlaid on 0.8% to 1% agar coated surface, In an embodiment of the present invention, the mammal used is a nude Immuno-compromised mouse.

In an embodiment of the present invention, the model is useful in stimulating the progression of primary tumor formation.

In an embodiment of the present invention, the model is useful for assessing metastasis.

In an embodiment of the present invention, the model is useful for assessing tumourigenesis.

In an embodiment of the present invention, the adhesion-deprived cell is injected subcutaneously.

In an embodiment of the present invention, the detection of transformation and tumorigenicity is done by using the adhesion-deprived cells.

In yet another embodiment of the present invention, the detection is effected in the peripheral blood of the immune deficient mouse.

In yet another embodiment of the present invention, the detection is effected in the bone marrow of the immune deficient mouse.

In yet another embodiment of the present invention, the tumour model system is useful for detecting multistage cancer.

In yet another embodiment of the present invention, the adhesion-deprived cell is injected subcutaneously.

In still another embodiment of the present invention, an assay for assessing the effect of a treatment for cancer comprising:
  a. applying the treatment to an immune deficient mouse bearing a tumor generated by implanting locally advanced or metastatic tissue or a cell suspension thereof from a human in the immune deficient mouse;
  b. determining the effect of the treatment on the growth of the tumor in said mouse.

In still another embodiment of the present invention, the use of the model system in identifying the progression of cancer at their multistage.

In still another embodiment of the present invention, the use of the model system in developing anti-tumour therapies and various cancer drugs at different stages of cancer.

In still another embodiment of the present invention, the use of the model system for identifying metastatic cells.

DETAILED DISCRIPTION OF THE INVENTION

The present invention achieves a method to develop transformed cells from normal adherent cells by depriving from adhesion. Transformed cells can grow as soft agar colonies in soft agar colony formation assay and tumors in nude mice. These cells have the capacity to metastasize by localizing at distant organs. The model system is very useful to study the progression of cancer at multiple stages and to screen the anti-cancer drugs at different stages.

EXAMPLES

The following examples are given by way of illustration of the present invention and therefore should not be construed to limit the scope of the present invention.

Example 1

Preparation of Adhesion Deprived Cells

F111 cells were trypsinized and suspended in DMEM containing 1.0% FCS, and plated on plastic or on 1% agarose coated surfaces a concentration of $2-3\times10^6$ cells in 5 ml and incubated at 37° C. and 5% $CO_2$ for different periods of time.

The cells on plastic are able to adhere and cells on agar remain adhesion deprived and are in suspension due to non-availability of the substratum.

Assay for Cell Viability

Adherent and adhesion deprived cells collected at different time points were checked for their viability by MTT assay.

Tumor Like Properties

Soft Agar Colony Formation $1\times10^5$ Adherent and adhesion deprived cells at different time points were suspended in 0.3% agarose in complete DMEM medium and overlaid on 0.8% coated surfaces. The Cells were allowed to grow for a weak and the colonies formed were counted.

Forming Tumors in Mice $5\times10^6$ adherent and adhesion deprived cells in 100 ul of PBS were injected subcutaneously in to a nude mouse of age of six weak and the size of the tumor is measured at different time points.

Identifying Metastatic Cells

Tumors developed after the injection of adhesion deprived cells were allowed to grow for a period of three months and tissue sections collected from tumor and lung were stained histopathologically.

Adhesion Deprived Cell Preparation

Figure 1:
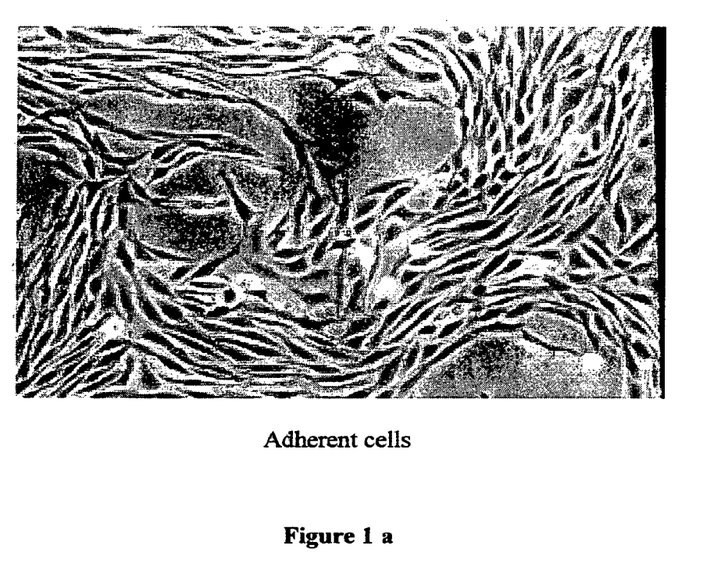
FIG. 1a. Figure includes the picture of Rat Fibroblast cell lines (F111). Spindle shaped cells are well spread and attached to the substratum.
FIG. 1b. The picture includes the non-adherent cells. Normal F111 cells are trypsinized and plated on 0.8% agarose coated surface.
Figure 1B:
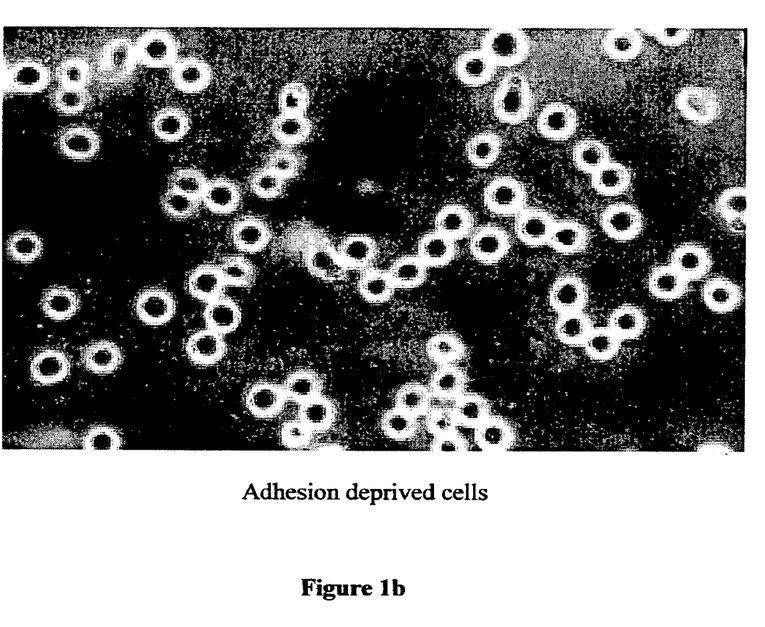

Results showed that cells on plastic are adherent to the substratum and are well spread. However the cells on agar remain adhesion deprived due to blockage of the surface and remain round by losing their shape. (FIG. 1a, 1b)

Example 2

Measurement of Cell Viability

Figure 2:
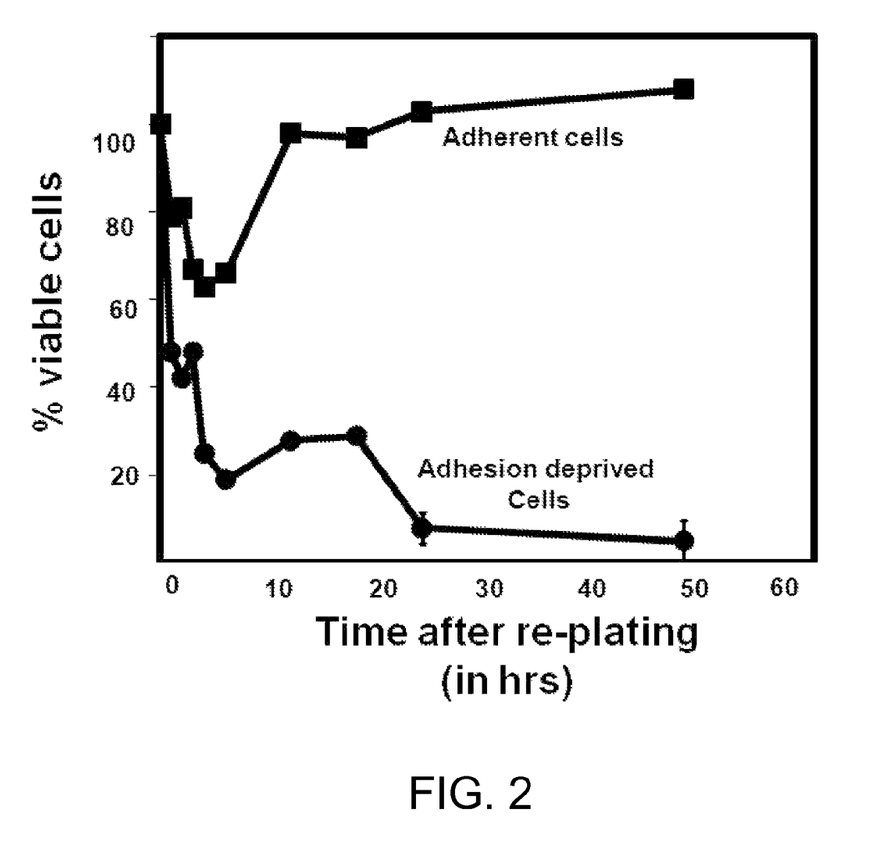
FIG. 2. The graph shows the percent cell viability of Adherent and non-adherent cells/adhesion deprived cells. The viability of the cells is checked by MTT assay at different time points.

Results obtained by MTT assay for the cell viability of adherent and adhesion deprived cells at different time periods showed that there was a continuous loss of cell viability with adhesion deprived cells due to non-availability of the substratum. However, adherent cells could pick up survival rate as they are well spread and adherent to a substratum. (FIG. 2)

Example 3

Formation of Colonies in Soft Agar

Figure 3A:
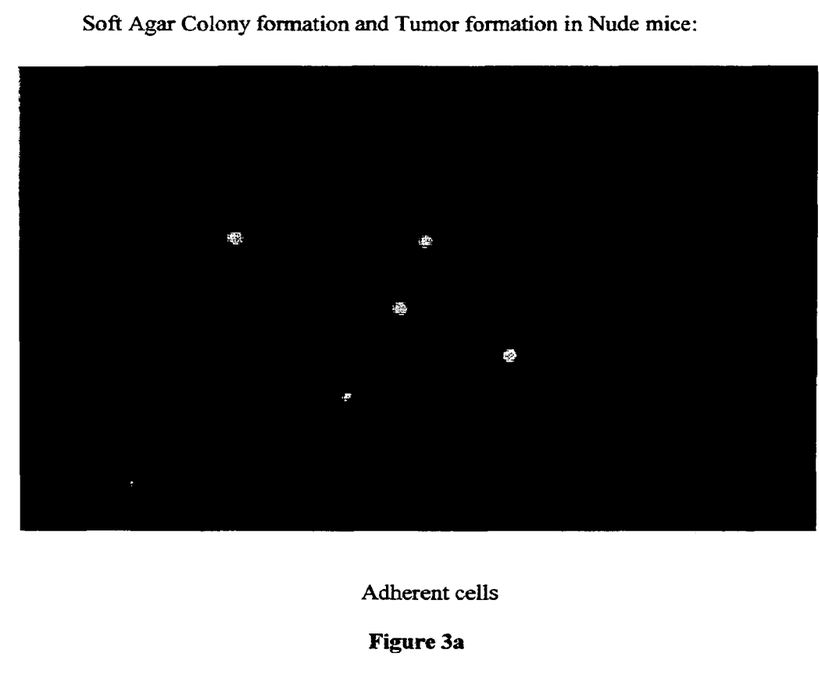
FIG. 3a. The picture shows the soft agar colony formation of adherent cells.
Figure 3B:
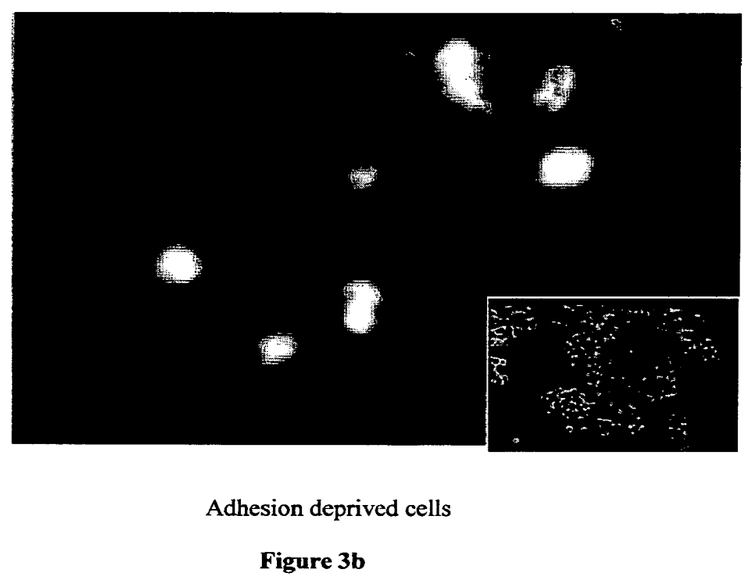
FIG. 3b. The picture includes the soft agar colony formation of non-adherent cells/adhesion deprived cells in soft agar colony assay.

Results from the picture indicate that the adhesion-deprived cells could form the colonies on soft agar as they are undergoing transformation during non adhesion period (FIGS. 3a and 3b).

Example 4

Formation of Tumors

Figure 4A:
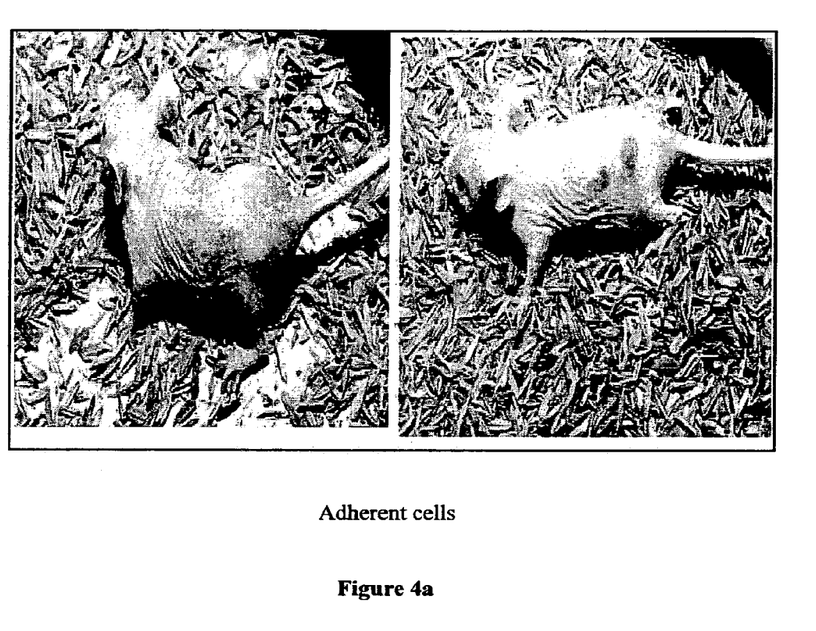
FIG. 4a. Tumor formation with adherent cells when injected subcutaneously in to nude mice.
Figure 4B:
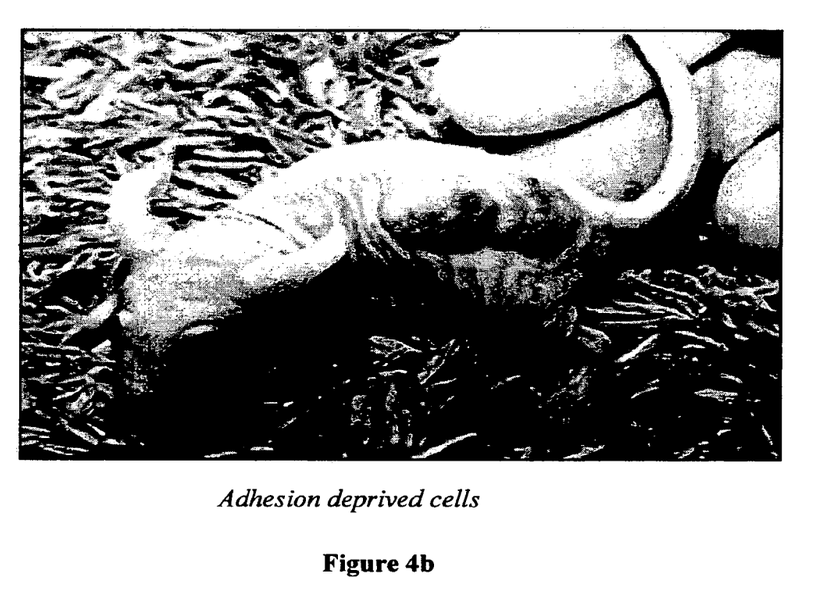
FIG. 4b. Tumor formation with non-adherent cells/adhesion deprived cells, when injected subcutaneously in to nude mice. Tumor is indicated with an arrow.
Figure 4C:
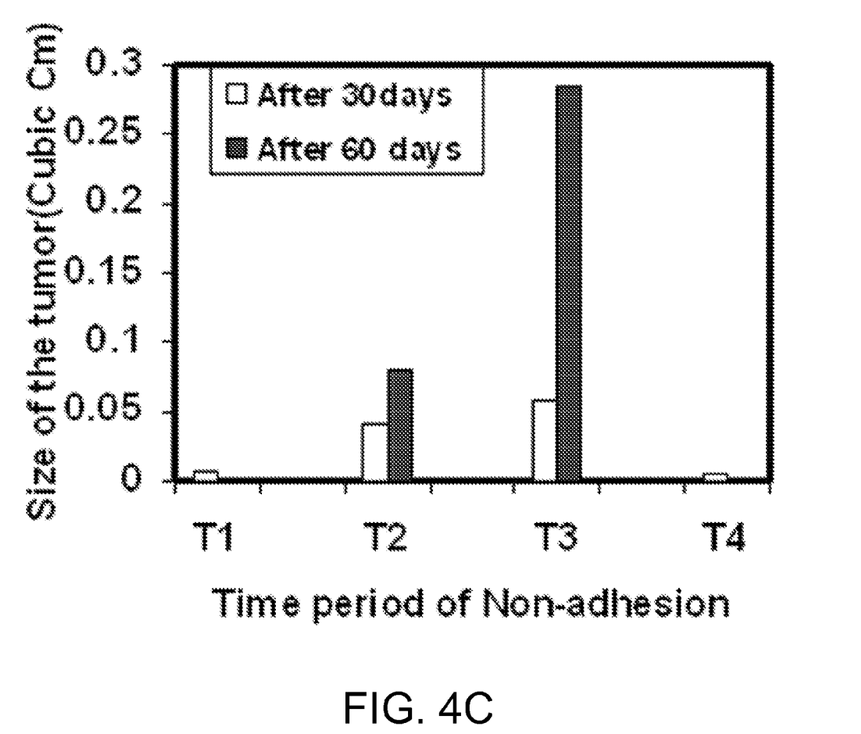
FIG. 4c. Graph includes the growth of tumor at different time points, after injecting in to nude mice.

The following picture shows that adhesion deprived cells have the potential to form tumors but not with adherent cells. Tumorigenicity increases with increase in time points of adhesion deprival period and later decreases. Tumor formation is very aggressive up to a certain time period and decreased further at later time points (FIG. 4a, 4b, 4c).

Example 5

Metastasis

The tissue sections of tumor and lung stained with Eiosin and Heamatoxilin showed that the adhesion deprived cells could metastasize at distant organs.

Figure 5A:
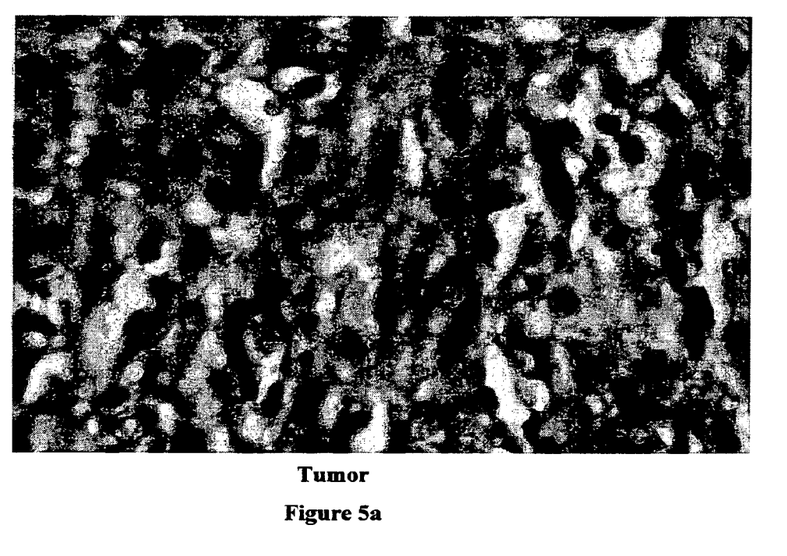
FIG. 5a. The figure includes the Heamatoxillin and Eosin staining of a tumor section. Tumor cells are indicated with arrow and are growing as spindle shaped, neoplastic and pleomorphic cells. The nucleus of these cells is darkly stained.
Figure 5B:
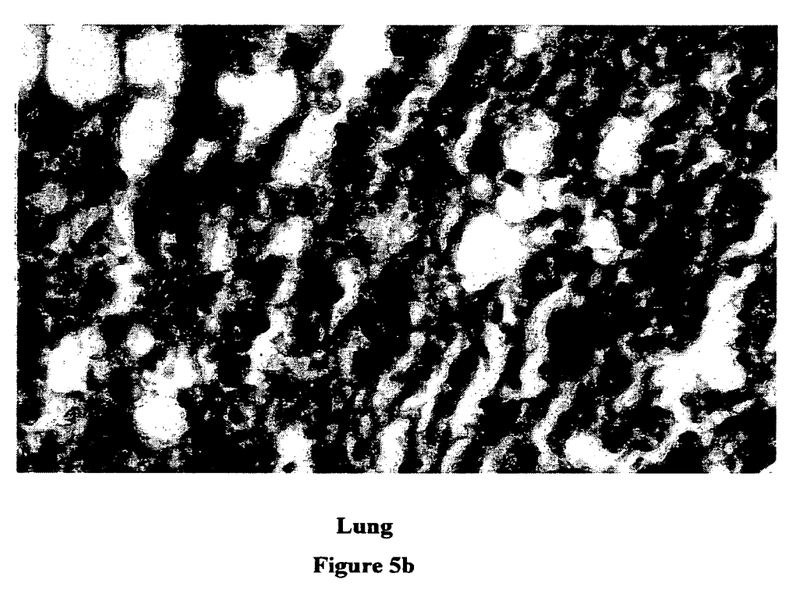
FIG. 5b. Heamatoxillin and Eosin staining pattern of a section from lung tissue. The spindle shaped cells, indicated with arrow are invading in to lung by occupying the alveolar region.

Results from the staining pattern indicate that the adhesion-deprived cells could migrate to distant organs, colonize by metastasis (FIGS. 5a and 5b).

Advantages

Reasons are not specific for numerous and diverse genetic alterations that accompany tumorigenesis and raises questions as to whether experimental cancer-promoting factors remain relevant to tumor maintenance. We have shown that the adhesion deprivation as one of causative factors involved in the process of transformation in in vivo and in vitro conditions. Though several model systems of cancer exist in various patents and literature, our current observations showed a tumor model system with adhesion deprived cells. This observation provides a new method for primary detection of transformation of adhesion-deprived cells and tumorigenicity.

Another advantage of the model system is that the adhesion-deprived cells are capable of metastasizing at distant sites.

As the model system includes both the tumor formation and metastasis, it is very important over the other models in the treatment of cancer with various drugs at different stages of cancer.

We claim:

1. A mouse tumor model system comprising adhesion deprived cells capable of metastasizing at one or more sites prepared by a method comprising:
    (a) trypsinizing normal adherent F111 rat fibroblast cells;
    (b) suspending the trypsinized F111 rat fibroblast cells on a surface coated with agarose in a medium containing Fetal Calf Serum (FCS) to obtain adhesion-deprived F111 rat fibroblast cells; and
    (c) administering subcutaneously the F111 adhesion-deprived rat fibroblast cells to an immunocompromised mouse to form tumors or to metastasize, or both to form tumors and to metastasize in the immunocompromised mouse;
    wherein the normal adherent F111 rat fibroblast cells are non-transfected cells.

2. The mouse tumor model system of claim 1, wherein the surface coated with agarose is further defined as a surface coated with about 0.8% agarose to about 1% agarose.

3. The mouse tumor model system of claim 1, wherein the adhesion-deprived cells form tumors or to metastasize, or both to form tumors and to metastasize, in the immunocompromised mouse about four weeks to about six weeks after administration.

4. The mouse tumor model system of claim 1, wherein the medium contains about 8% FCS to about 10% FCS.

5. The mouse tumor model system of claim 1, further comprising mixing the trypsinized cells with agarose in serum prior to suspending the cells on a surface coated with agarose.

6. The mouse tumor model system of claim 5, wherein the trypsinized cells are mixed with about 0.2% to about 0.3% agarose in serum prior to the suspending.

7. The mouse tumor model system of claim 1, wherein the immunocompromised mouse is a nude mouse.

8. The mouse tumor model system of claim 1, wherein administering subcutaneously the adhesion-deprived cell is by injection.

9. A method comprising:
    (a) obtaining a mouse tumor model system of claim 1;
    (b) applying an anti-cancer treatment to the mouse tumor model system; and
    (c) determining the effect of the anti-cancer treatment on growth of the adhesion-deprived cells that are forming tumors or metastasizing, or both forming tumors and metastasizing, in said immunocompromised mouse of the tumor model system.

10. The mouse tumor model system of claim 1, wherein the immunocompromised mouse comprises a tumor or metastatic cells.

* * * * *